(12) United States Patent
Delorme et al.

(10) Patent No.: US 9,649,253 B2
(45) Date of Patent: May 16, 2017

(54) KIT FOR PRESERVING A BIOLOGICAL PRODUCT INCLUDING A THREE-DIMENSIONAL BAG AND A MATCHING THREE-DIMENSIONAL CASING

(75) Inventors: Bruno Delorme, Marcq-en-Baroeul (FR); Marie Plainfosse, Marcq-en-Baroeul (FR)

(73) Assignee: Maco Pharma, Mouvaux (FR)

( * ) Notice: Subject to any disclaimer, the term of this patent is extended or adjusted under 35 U.S.C. 154(b) by 708 days.

(21) Appl. No.: 14/131,399

(22) PCT Filed: Jul. 3, 2012

(86) PCT No.: PCT/FR2012/051553
§ 371 (c)(1),
(2), (4) Date: Jan. 7, 2014

(87) PCT Pub. No.: WO2013/007921
PCT Pub. Date: Jan. 17, 2013

(65) Prior Publication Data
US 2014/0144800 A1 May 29, 2014

(30) Foreign Application Priority Data
Jul. 8, 2011 (FR) ..................... 11 56212

(51) Int. Cl.
| A61B 19/00 | (2006.01) |
| A61J 1/10 | (2006.01) |
| A01N 1/02 | (2006.01) |
| A61J 1/16 | (2006.01) |
| A61J 1/12 | (2006.01) |
| A61B 5/15 | (2006.01) |

(52) U.S. Cl.
CPC .............. *A61J 1/10* (2013.01); *A01N 1/0263* (2013.01); *A01N 1/0268* (2013.01); *A61B 5/150038* (2013.01); *A61J 1/12* (2013.01); *A61J 1/16* (2013.01)

(58) Field of Classification Search
CPC ........ A61J 1/10; A61J 1/05; A61J 1/12; A61J 1/165; A61J 1/16; A61M 1/0272; F25C 1/243; A61B 5/150038; A01N 1/0263; A01N 1/0268
See application file for complete search history.

(56) References Cited

U.S. PATENT DOCUMENTS

| 3,042,086 A * | 7/1962 | Winchell ................. A61J 1/10 141/390 |
| 4,090,374 A * | 5/1978 | Faust .................... A61J 1/1462 206/451 |
| 2004/0254560 A1 * | 12/2004 | Coelho .................... A61J 1/05 604/408 |

* cited by examiner

*Primary Examiner* — Tatyana Zalukaeva
*Assistant Examiner* — Ariana Zimbouski
(74) *Attorney, Agent, or Firm* — IP Attorneys Group, LLC

(57) ABSTRACT

The invention relates to a kit for preserving a biological product including a three-dimensional bag (1) intended for holding said biological product, said bag (1) having a substantially constant three-dimensional geometry during the use thereof, as well as a casing (2) intended for packing said bag, said casing (2) including a cavity (3) arranged such as to receive said bag (1), said cavity (3) having a substantially constant three-dimensional geometry during the use thereof, and a slot (4) being provided along one edge of said cavity such as to enable said bag (1) to be inserted in said cavity (3), a front strip (5) and a rear strip (6) extending on the outside away from said slot (4), said strips being intended for being combined with one another in order to provide an airtight seal of said cavity (3) of the casing (2).

16 Claims, 8 Drawing Sheets

KIT FOR PRESERVING A BIOLOGICAL PRODUCT INCLUDING A THREE-DIMENSIONAL BAG AND A MATCHING THREE-DIMENSIONAL CASING

CROSS REFERENCE TO RELATED APPLICATIONS

This application is a national phase filing of pending International Application No. PCT/FR2012/051553 filed on Jul. 3, 2012 titled "KIT FOR PRESERVING A BIOLOGICAL PRODUCT INCLUDING A THREE-DIMENSIONAL BAG AND A MATCHING THREE-DIMENSIONAL CASING", which claims priority of French Patent Application No. 1156212 filed on Jul. 8, 2011. The contents of the above-identified applications are relied upon and incorporated herein by reference in their entirety.

The invention relates to a kit for preserving a biological product including a three-dimensional bag and a casing intended to receive said bag.

The invention applies in general to the preservation of liquid or semi-liquid biological products such as blood, blood components, cells, or biological tissues. The invention applies in particular to the cryopreservation of umbilical cord blood, vaccines or conditioned cell culture mediums.

Umbilical cord blood contains a large number of stem cells, in particular hematopoietic stem cells which are at the origin of the various cells of the blood: red blood cells, white blood cells and platelets. These cells participate in the defence of the organism (immune system). As such and since the first cord blood transplant in 1988, cord blood transplants have become an alternative to bone marrow transplants and are increasingly used. In addition, the presence in cord blood of other cells of interest, such as mesenchymal stem cells, multipotent stem cells, and immune system cells, opens the door to other applications in regenerative medicine (treatment for diabetes, myocardial infarction, neurodegenerative diseases, etc.) as well as in immunotherapy.

In order to meet the increasing need for umbilical cord blood, banks intended to preserve this blood have been created. After sampling a unit of cord blood using a bag system such as described in document EP-1 262 202, and after a step referred to as "volume reduction", the unit of cord blood treated as such is transferred into a freezing bag. The freezing bag is then placed in a metal cassette which is finally plunged into liquid nitrogen for preservation. Alternatively, the bag is plunged directly into the liquid nitrogen.

Three-dimensional bags that can resist extreme temperatures and which allow for uniform freezing/thawing in order to prevent damage to the cells have been developed. Such bags are described in documents WO-97/49959, WO-2004/108057 and WO-98/09872.

Today, in order to prevent the risks of cord blood leaking during its preservation and prevent cross-contamination between several units of cord blood preserved in the same container of liquid nitrogen, the freezing bag is first placed in a casing that is hermetically sealed before possibly being placed in the metal cassette. As such, if a bag is pierced, the blood flows in the hermetical casing without soiling the other bags. This procedure is for example described in document WO-2010/119311.

A casing for protecting a storage bag is described in document EP-A1-1 864 641. The casing is comprised of a relatively thin film comprising an adhesive layer of a fluoropolymer.

This type of two-dimensional casings is poorly adapted to cord blood storage bags. Firstly, it is not easy to slide the storage bags into these casings of which the dimensions are adjusted to the dimensions of the bags.

Then, the casing creates an additional thickness in such a way that it is not easy to place the bag and casing unit in a metal cassette.

Finally, before the casing is closed, it is necessary to carry out the elimination or reduction of the quantity of air retained between the bag and the casing. Indeed, this quantity of air can hinder the freezing and the thawing of the unit of cord blood and cause damage to the cells of interest contained in the cord blood. In addition, and in order to optimise the storage spaces as much as possible, metal cassettes can have dimensions adjusted to those of freezing bags. Therefore, an excessive quantity of air increases the volume of the bag and casing unit, which can then result in disturbing the setting into place of the freezing bag into the metal cassette.

The invention proposes a kit comprising a storage bag and a suitable casing making it possible to more easily insert the bag into its casing. The bag and casing unit is then easily placed in a metal cassette for freezing.

To this effect, the invention proposes a kit for preserving a biological product comprising on the one hand a bag intended to hold said biological product, said bag having a substantially constant three-dimensional geometry during the use thereof, and on the other hand a casing intended to pack said bag, said casing including a housing arranged such as to receive said bag, said housing having a substantially constant three-dimensional geometry during the use thereof, and a slot being provided along one edge of said housing such as to enable the bag to be inserted in said housing, a front strip and a rear strip extend on the outside away from said slot, said strips being intended to be combined with one another in order to hermetically seal said housing of the casing.

Other objects and advantages shall appear in the following description.

The invention relates to a kit for preserving a biological product comprising on the one hand a bag intended to hold said biological product and on the other hand a casing intended to pack said bag.

A biological product is for example blood, a blood component such as serum, plasma, platelets, white blood cells, red blood cells, a buffy coat, a platelet lysate, or bone marrow.

Other examples of biological products are products comprising enzymes such as trypsin, cell lines, cells associated with matrices of the nano-, macro-matrix or mini-bead type, supernatants of interest of cellular products, or vaccines.

Biological products also include culture mediums, whether or not conditioned, solutions for preserving organs, tissues and/or cells, and blood substitutes (synthetic haemoglobin) and biopharmaceutical molecules.

In particular, the biological product comprises human or animal cells, in particular cells for therapeutic use such as stem cells.

More specifically, the biological product to be preserved is a reduced unit of cord blood, i.e. a volume of cord blood sampled, after the birth of the baby, from an umbilical cord, and which has been treated for example by centrifugation and/or addition of starch (HES, hydroxyethylstarch) in order to obtain a smaller volume of cord blood devoid of red blood cells and enriched with cells of interest.

In an alternative, an additive is added to the biological product, such as a cryoprotectant agent of the DMSO (dimethyl sulphoxide) and/or glycerol type.

The preservation of the biological product is carried out at various temperatures (4° C., −20° C., −80° C.) and in particular by freezing the biological product then storing in liquid nitrogen at −196° C.

To preserve a biological product of the cord blood type, it is known to use three-dimensional bags carried out by moulding, as described in the abovementioned patent documents.

Contrary to two-dimensional bags, carried out for example using two substantially planar sheets connected together on their periphery or a sheath of which the ends are closed, which, when they are empty, are substantially flat, empty three-dimensional bags are not flat and have a certain relief.

According to the invention, the bag of the kit has a substantially constant three-dimensional geometry during the use thereof.

Figure 1:
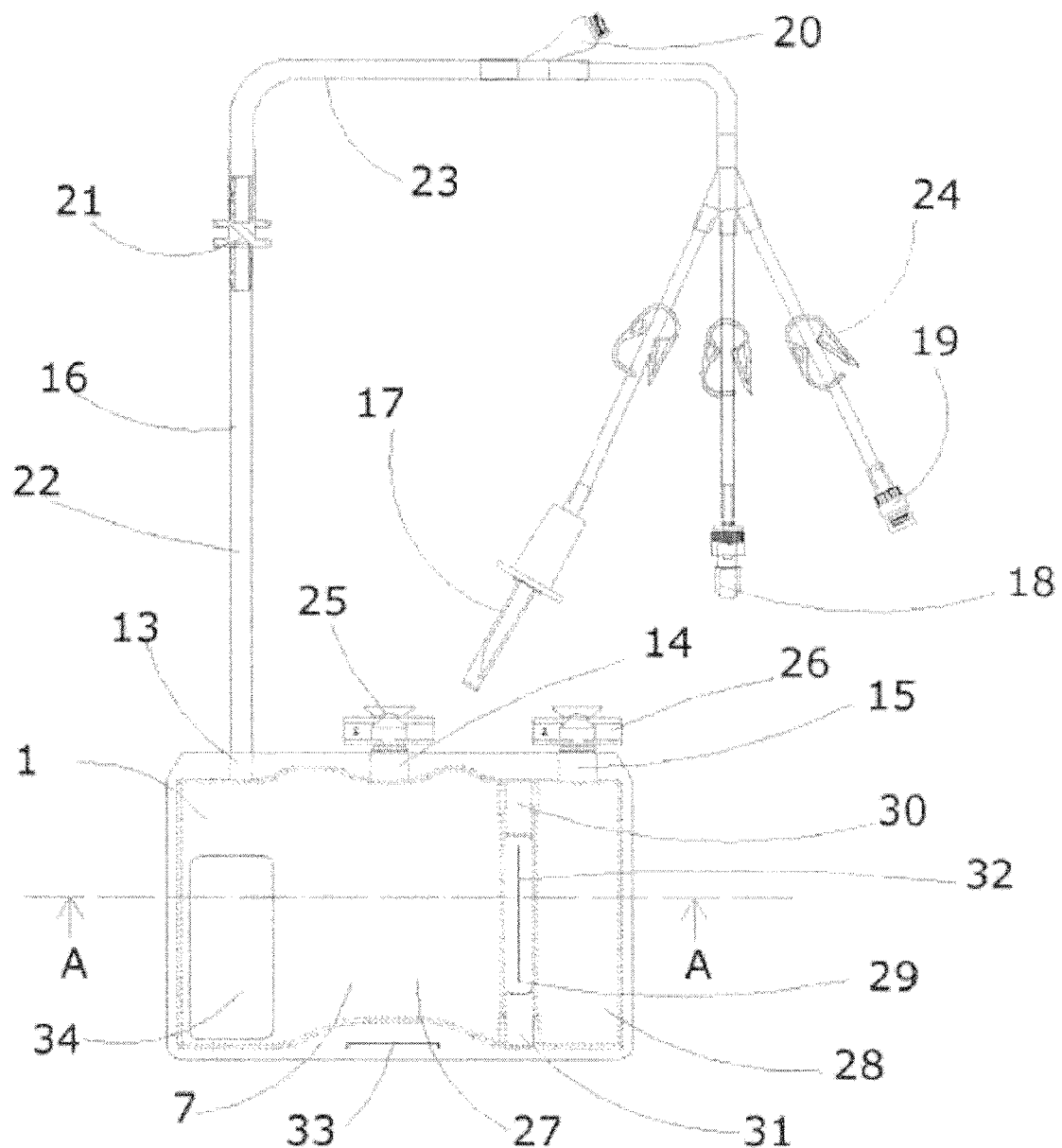
FIG. 1 diagrammatically shows a front view of a three-dimensional bag provided with a tubing and connectors.
Figure 2:
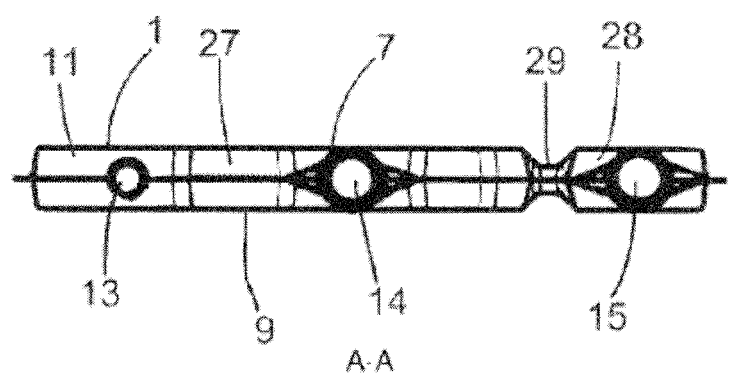
FIG. 2 diagrammatically shows a cross-section view according to the line AA of the bag of FIG. 1.

Such a bag is shown in FIGS. 1 and 2. The bag 1 has a substantially constant three-dimensional geometry during the use thereof, i.e. in particular the bag does not inflate when it is filled with a liquid. The geometry of the bag is fixed at the time of manufacture by giving a predefined shape to the bag. The bag retains its original geometry when it is filled with the biological product to be preserved and when it is stored.

In FIGS. 1 and 2, the bag 1 substantially has the shape of a parallelepiped rectangle, i.e. a parallelepiped of which the 6 faces are rectangles.

Contrary to a two-dimensional bag which changes geometry as it is filled with a liquid, the geometries of the three-dimensional bag empty and filled with the biological product to be preserved are substantially identical.

During the preservation of the bag, it is advantageous to overpack said bag in a casing 2 and to seal it hermetically in order to prevent a leak in a bag from producing contamination of the other bags stored in the vicinity of it.

Figure 3:
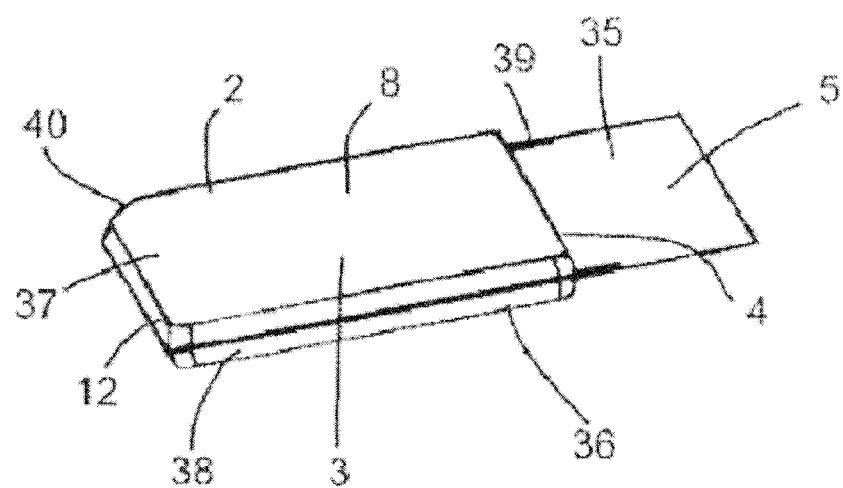
FIG. 3 diagrammatically shows a perspective view of the casing for housing the three-dimensional bag shown in FIG. 1 according to a particular embodiment.

According to the invention and as illustrated in FIG. 3, the casing 2 intended to pack said bag comprises a housing arranged such as to receive said bag 1. This housing has a substantially constant three-dimensional geometry during the use thereof, i.e. the housing is not deformed when the bag is inserted therein. The housing of the casing has a substantially identical geometry when it is empty or when it contains the bag. This geometry is determined at the time of manufacture, by giving a predefined shape to the housing.

A slot 4 is provided along one edge of said housing 3 in order to enable the bag to be inserted in said housing, a front strip 5 and a rear strip 6 extend on the outside away from said slot 4. These strips 5, 6 are intended to be combined with one another in order to hermetically seal said housing 3 of the casing 2, once the bag is placed in said housing 3 of the casing 2.

These strips 5, 6 further make it possible to more easily open the slot 4 of the casing in order to facilitate the inserting of the bag into its housing 3.

Once the bag is placed in the housing 3, the strips 5, 6 are combined with one another, in particular by welding, in order to close the slot 4. The strips 5, 6 are then separated from the casing 2.

The inside dimensions of the geometry of the housing 3 substantially correspond to the outside dimensions of the geometry of said bag 1 to be placed in the housing 3, in order to minimise the space, and therefore the volume of air, between the casing 2 and the bag 1 once the bag is housed in the housing.

Indeed, the presence of air disturbs the proper unfolding of the freezing and of the thawing of the bag and can result in the damaging of the cells of interest. With dimensions adjusted as such, the volume of air between the bag and its housing is minimal, which makes it possible to optimise the preservation of the biological product.

Furthermore, with casing/bag dimensions adapted as such, the presence of the casing around the bag does not have a substantial impact on the space occupied by the unit formed by the casing and the bag. Indeed, the presence of the casing does not hinder the inserting of the bag into a metal cassette for freezing.

Structurally, the bag 1 and the housing 3 are formed respectively of a substantially planar front face 7, 8 and rear face 9, 10, connected together by lateral walls 11, 12, with each of said faces and said walls of the bag and of said housing being intended to be arranged across from one another.

The slot 4 of the casing is provided on one of said lateral walls 12 of the housing, in particular on the longest lateral wall.

As shown in FIGS. 1 and 2, the bag 1 comprises on one of the lateral walls at least one inlet orifice 13 and/or outlet orifice 14, 15 of the biological product. In particular, all of the inlet/outlet orifices 13-15 are arranged on the same lateral wall 11 in order to reduce the dimensions of the bag 1 as much as possible.

In particular, the bag 1 comprises an inlet orifice 13 for the introduction of the biological product into the bag. This orifice is connected to the end of a tubing 16. The other end of the tubing is connected to one or several means 17, 18, 19 for connecting to bags or syringes, such as connectors of the perforator 17, male luer 18, female luer or needleless self-sealable connector 19 type.

As shown in FIG. 1, the tubing 16 is also provided with an injection site 20 in the form of a self-sealable luer, in order to, for example, provide an additive to the biological product.

As an alternative embodiment, the tubing 16 comprises a connector 21 for connecting portions of tubing made of different materials. In FIG. 1, the connector 21 makes it possible to connect the portion of tubing 22 connected to the bag and made of ethylene vinyl acetate to the other portion of tubing made of polyvinyl chloride 23.

The tubing 16 is also provided with one or several selective means 24 for closing and/or opening fluidic communication in the tubing 16. Such means are for example clamps or open-circuits.

An outlet orifice 14, 15, separate from the inlet orifice 13, is advantageously provided to empty the biological product after preservation, at the time it is used. The outlet orifice 14, 15 is formed by a portion of tubing closed by a vane 25, 26. In order to access the orifice 14, 15, it suffices to apply a movement of rotation to the vane 25, 26 in order to separate it from the bag.

The bag 1 comprises one or several compartments. The number and the surface of the various compartments vary according to the volume that has to be contained in each of the compartments defined. According to a particular embodiment, the bag 1 comprises at least two compartments 27, 28 separated by a partition 29. The partition is formed by a weld between the two compartments 27, 28. In particular, the partition 29 is interrupted at one or several locations 30, 31 in order to allow for fluidic communication between the various compartments 27, 28. More particularly, the interruptions 30, 31 are located at the ends of the partition.

Furthermore, the partition 29 advantageously comprises a slot 32 in order to facilitate the separation of the compartments 27, 28 where applicable.

As shown in FIG. 1, each compartment 27, 28 comprises an outlet orifice 14, 15, in particular in the form of a portion of tubing closed by a vane 25, 26.

After having introduced the biological product into the three-dimensional bag 1, the tubing 16 is closed and cut off, in particular by weld, in order to separate the bag 1 from the portion of tubing comprising the connectors 17-19 and other elements such as the connector 21 and the injection site 20.

A portion of tubing connected to the inlet orifice of the bag is advantageously retained in order to carry out a sampling of the biological product contained in the bag. To do this, the portion of tubing filled with biological product is divided into two or several segments of tubing each comprising a sample of biological product. The segments are in particular carried out by welding.

The housing 3 of the casing 2 has dimensions that are sufficient to pack the bag 1 provided with its inlet 13 and/or outlet 14, 15 orifices and possibly the portion of tubing used for the sampling.

The bag 1 comprises a slot 33 making it possible to suspend the bag 1 during the perfusion of the biological product to a patient. Advantageously, the slot 33 is arranged facing the outlet orifice or orifices 14, 15 of the bag 1. The suspension slot 33 is more particularly positioned on the peripheral seal of the bag, on an enlargement of said seal.

In FIG. 1, the bag 1 comprises a label 34 in order to provide identification and traceability for the biological product to be preserved.

The internal volume of the bag is comprised between 1 ml and 1 L, particularly between 5 and 50 ml, and more particularly approximately 25 ml. When the bag 1 is intended to preserve a unit of cord blood, its internal volume is comprised between 5 and 50 ml, in particular 25 ml.

According to a particular embodiment of the invention, the casing 2 is formed of a first sheet 35 and of a second sheet 36, with at least one of the sheets having a relief 37, 38 forming at least one portion of the housing 3 for the bag 1, with the two sheets 35, 36 being assembled together along a peripheral seal 39 surrounding said relief, with the peripheral seal 39 having an interruption in order to form the slot 4 of the casing 2.

As shown in FIG. 3, the peripheral seal 39 is extended over a portion of the periphery of the strips 5, 6. Advantageously, the peripheral seal is extended over a portion only of the strips 5, 6. As such, the strips 5, 6 are separated easily in order to enable the opening of the slot 4 and the inserting of the bag 1. And the extension of the peripheral seal 39 secures the peripheral seal of the casing by creating a point of weakness separated from the relief 37, 38 forming the housing 3.

The relief 37, 38 has a substantially planar surface corresponding to the front 8 or rear 10 face of the housing 3 of the casing 2 and an edge surrounding said surface corresponding to at least a portion of the lateral walls 12 of the housing 3.

Figure 4:
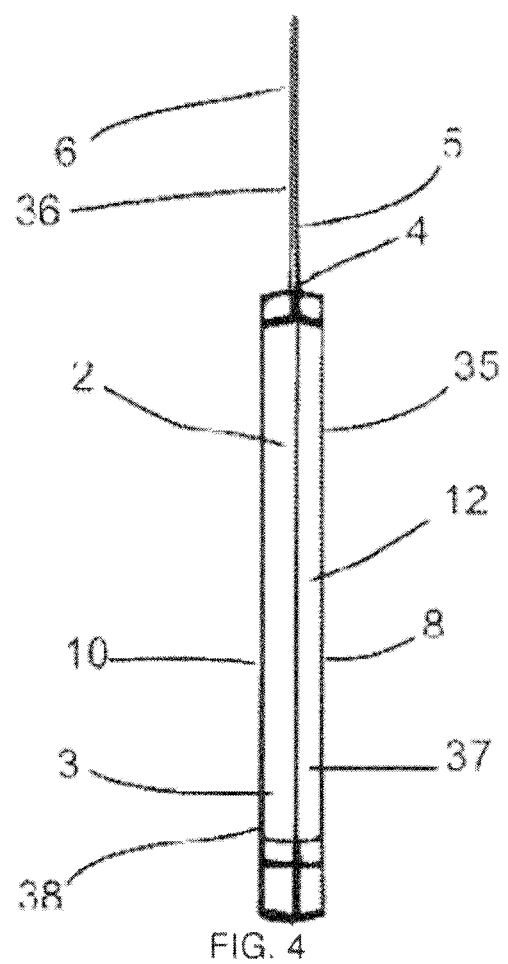
FIG. 4 diagrammatically shows a side view of the casing of FIG. 3.
Figure 5:
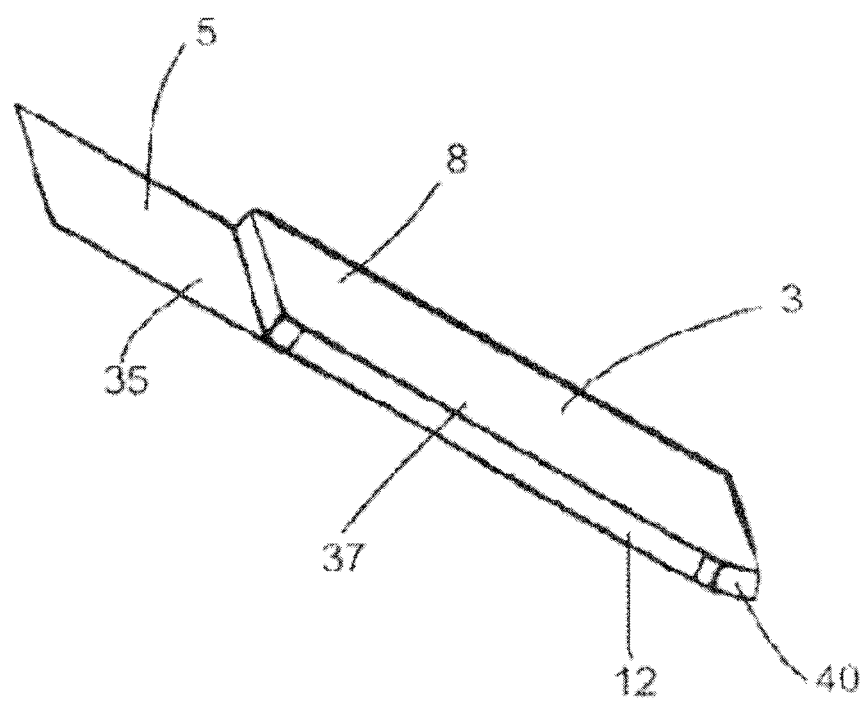
FIGS. 5 and 6 diagrammatically show a top and bottom view respectively, and in perspective, of one of the thermoformed sheets constituting the casing of FIG. 3.
Figure 6:
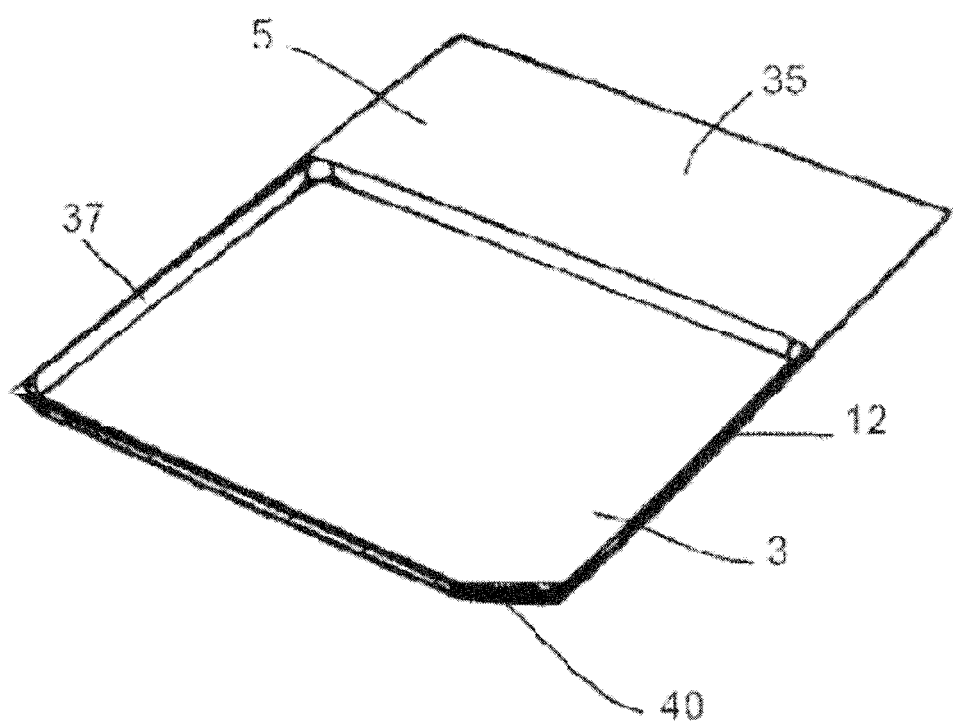

In FIGS. 4 to 6, the edge is substantially perpendicular to the planar surface of the relief 37. As such, the relief has a parallelepiped shape of which each of the faces is substantially rectangular. The angles between on the one hand the different lateral faces forming the edge and on the other hand the faces forming the planar surface and the lateral faces are rounded or blunted.

In FIGS. 3 and 5 to 7, one of the lateral edges of the parallelepiped relief 37 has a chamfer 40 obtained by cutting the edge in such a way as to withdraw a portion in the shape of a triangular prism and in such a way as to reduce the space between the bag 1 and the housing 3, when the bag 1 is in the housing 3 of the casing 2.

Figure 8:
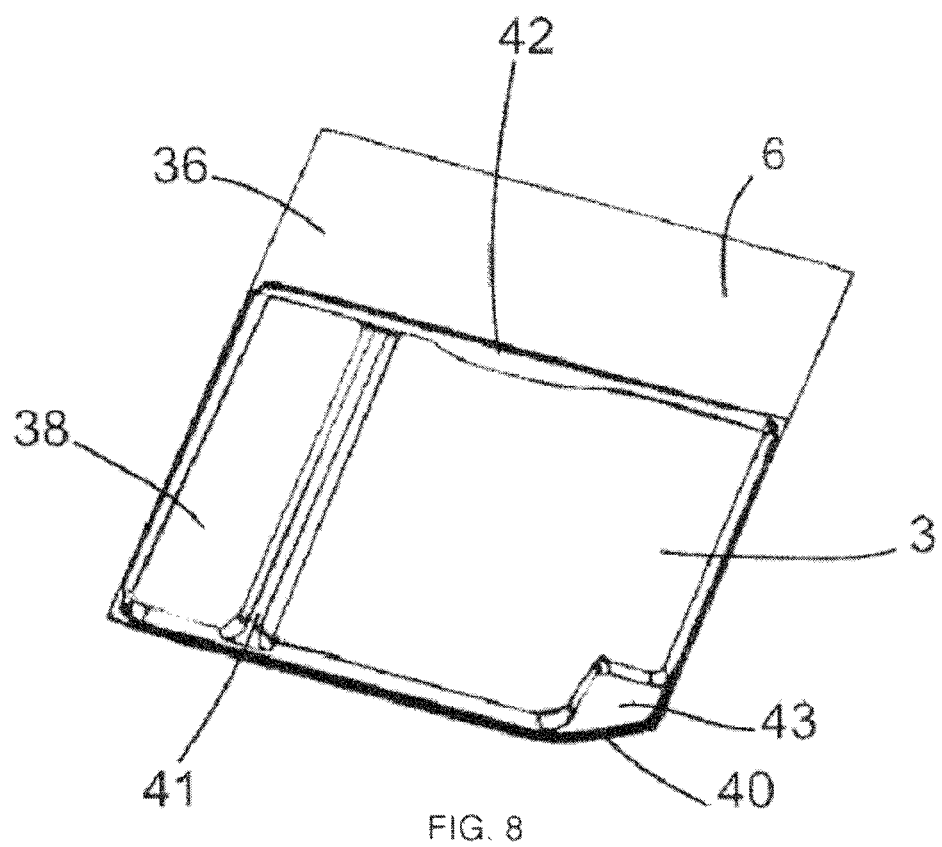
FIG. 8 diagrammatically shows a perspective view of a sheet of a casing as shown in FIG. 3 according to another particular embodiment.

As shown in FIG. 8, the relief 38 of one of the sheets 36 at least comprises one or several cavities 41, 42, 43 corresponding to the geometry of the three-dimensional bag 1.

For example, the relief 38 comprises a cavity 41 that corresponds substantially to the partition 29 of the bag 1. The cavity 41 has the shape of a straight notch passing through the relief. The cavity is made on the face corresponding to the front 8 or rear 10 face of the housing of the casing 2 and extends between two lateral walls opposite the housing 3. The depth of the notch is equal to or slightly less than the height of the relief 38.

Alternatively or additionally, the relief 38 comprises a semi-oval cavity 42 corresponding to the enlargement of the peripheral seal of the bag, at the location where the suspension slot 33 is arranged.

Alternatively or additionally and aiming to further minimise the space between the bag and the casing, a cavity 43 in the shape of a triangle is arranged on the chamfer 40 cut from the relief 38.

These different cavities 41, 42, 43 render the reliefs 37, 38 of each of the sheets 35, 36 dissymmetrical, in such a way that the bag 1 can be inserted only in the direction that can make the cavities 41, 42, 43 of the relief correspond with those of the bag 1. As such, in the figures, the bag 1 is placed in the housing 3 in such a way as to arrange the orifices 13, 14, 15 of the bag in the bottom of the housing 3 of the casing 2, i.e. opposite the slot 4 for inserting.

According to a first embodiment not shown in the figures, only one of the sheets comprises a relief. In this case, the other sheet is planar.

According to another embodiment shown in the figures, the two sheets 35, 36 have a relief 37, 38. The relief 37, 38 of each of the sheets is identical or different.

In particular, according to an alternative, one of the sheets 36 comprises at least one cavity 41 that corresponds to the partition 29 of the bag, and the other sheet 35 does not comprise a cavity that corresponds to the partition of the bag.

Figure 7:
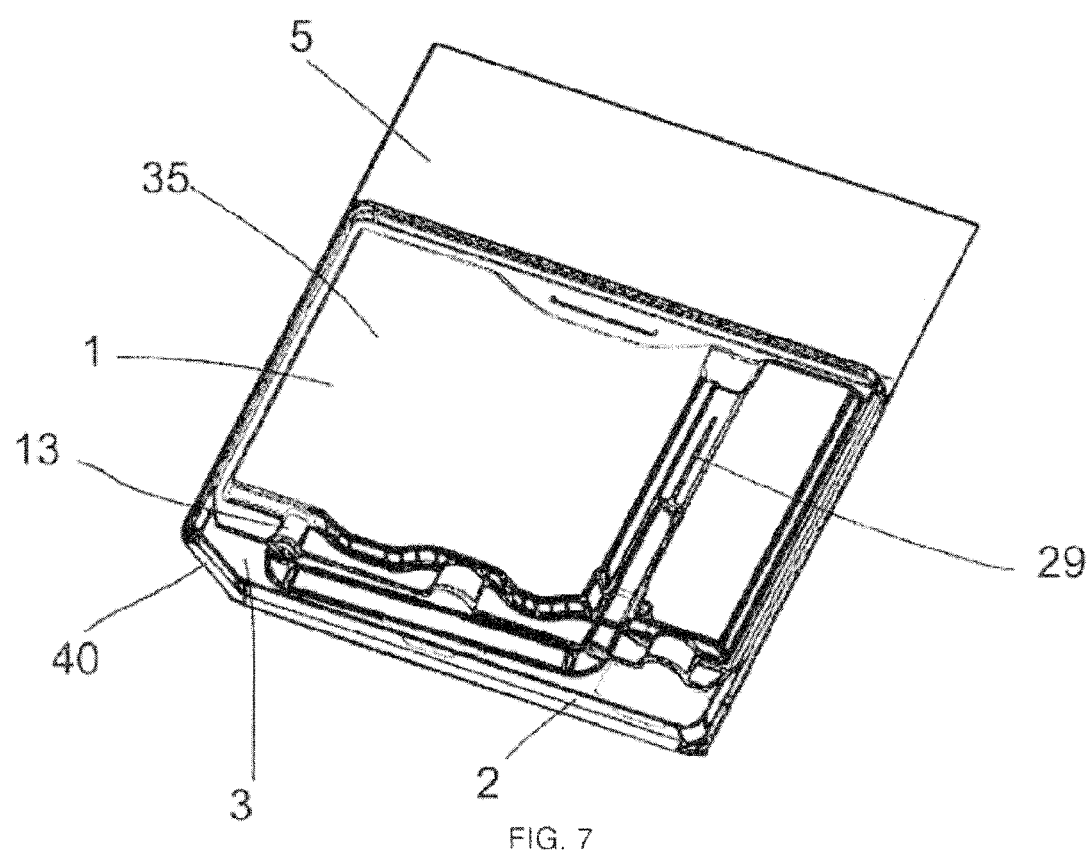
FIG. 7 diagrammatically shows a perspective view of the bag of FIG. 1 placed in the casing of FIG. 3.

The free space between the sheet 35 and the partition 29 of the bag 1 is then used advantageously to place, where applicable, the portion of tubing connected to the inlet orifice 13 of the bag and used for the sampling (FIG. 7).

The thickness of each of the sheets 35, 36 forming the casing 2 is comprised between 0.20 and 0.70 mm, in particular 0.35 mm. This thickness makes it possible to obtain a sufficient resistance, in particular in order to prevent a rupture during freezing.

According to an embodiment, the relief 37, 38 of the sheet forming the casing is carried out using a mould. In particular the relief of the sheet forming the casing is carried out by thermoforming. Other possible embodiments are extrusion blow-moulding or vacuum moulding.

In particular, each of the two sheets 35, 36 comprises a relief 37, 38 carried out by thermoforming.

The thermoformed sheet or sheets 35, 36 are carried out in a flexible thermoplastic material.

Flexible thermoplastic materials that can be thermoformed and welded are for example ethylene vinyl acetate, polyethylene or fluoropolymer such as a fluorinated ethylene propylene.

For example, the casing 2 and/or the bag 1 are carried out in ethylene vinyl acetate, polyethylene or fluoropolymer such as a fluorinated ethylene propylene.

In particular, the bag 1 and the casing 2 are carried out in the same material such as ethylene vinyl acetate.

The films made of ethylene vinyl acetate generally have a smooth face and a slightly rough face. This material is known to adhere easily. In order to prevent the bag from adhering to the casing, two smooth faces must be prevented from coming into contact. As such, it is advantageous to provide that the outside surface of the bag corresponds to the smooth face of the film made of ethylene vinyl acetate, and that the inside surface of the casing corresponds to the slightly rough face of the film made of ethylene vinyl acetate.

In order to comply with sanitary requirements in particular, the bag and the casing are packed separately and in a sterile manner. Alternatively, the bag and the casing are packed together and in a sterile manner.

Hereinafter is described a method for preserving a biological product using a kit according to the invention. The method comprises the steps consisting in:
- filling the three-dimensional bag 1 with the biological product to be preserved,
- placing the bag 1 filled as such in the housing 3 of said casing 2,
- combining the strips 5, 6 of the casing 2 with one another in such a way as to hermetically seal the housing 3 of the casing containing said bag 1,
- storing the bag 1 placed in the housing of the casing in suitable conditions in order to preserve said biological product.

The filling of the bag 1 is carried out by the intermediary of one of the connectors 17, 18, 19 provided on the tubing connecting to the inlet orifice 13 of the bag 1 or by sterile connection of the tubing 16 with another tubing connected to a source of biological product.

As the bag 1 is three-dimensional, it contained a certain volume of air that it is preferable to remove in order to allow for the filling of the bag with the biological product to be preserved. To do this, it is possible to connect an empty syringe to one of the connectors 17, 18, 19, then to aspirate the air contained in the bag using the syringe. Once this operation has been carried out, the biological product can be transferred to the bag 1, by gravity in particular.

The method of preservation can provide to place an additive such as a cryoprotectant agent with the biological product contained in the bag. This additive is for example dimethyl sulfoxide. The adding of the additive is carried out by the intermediary of one of the connectors 17, 18, 19 provided on the bag.

It is advantageous to remove the air contained in the bag before freezing in order to avoid damaging the cells during freezing. This operation is carried out using a syringe, by placing the bag in such a way as to bring the air bubble on the inlet orifice of the bag. The air is then aspirated by the syringe.

To carry out the sampling, where applicable, of the biological product contained in the bag, a portion of the biological product is maintained in the tubing connected to the bag during the aspiration of air or the filling of the bag.

When the biological product possibly containing the additive is in the bag, the portion of tubing connected to the inlet orifice 13 of the bag 1 is welded and cut. The portion of tubing comprising the connectors 17, 18, 19 is discarded. The other portion remained linked to the bag 1 is closed at several locations in order to form segments of tubing, for example two or three segments, each comprising a sample of biological product.

The filled bag is then placed in the housing 3 of the three-dimensional casing 2 by the intermediary of the slot 4.

Where applicable, the sampling tubing is folded along the lateral wall comprising the inlet/outlet orifices 13, 14, 15 and in the partition 29 between the two compartments 27, 28.

In order to facilitate the inserting of the bag 1, it is advantageous to fold a portion of the bag 1 back over itself before the inserting, then to slide the bag 1 folded as such in the housing 3 of the casing 2 until the bottom of said housing 3, and finally to unfold the bag 1 arranged in the housing 3.

Thanks to the consistent geometries of the bag 1 and of the casing 2, and in particular of the cavity or cavities 41, 42, 43 of the relief 37, 38, the bag 1 comes to place itself correctly in the housing 3 of the casing 2.

If one of the sheets of the casing 36 comprises a cavity 41 corresponding to the partition 29 of the bag 1 and not the other sheet 35, attention will be given to arranging the sampling tubing facing the sheet of the casing 35 that does not include a cavity corresponding to the partition 29 of the bag.

Once the bag 1 is filled and in place in the housing 3, the strips 5, 6 of the casing 2 should be combined with one another in such a way as to hermetically seal the housing 3 of the casing 2 containing said filled bag 1.

This step of sealing the housing 3 is carried out in particular by welding. The marking of the location where the weld must be carried out can be easily identified visually since the slot 4 is located at the interface of the housing 3 in relief and strips 5, 6.

Furthermore, as the space between the bag 1 and the housing 3 is minimal, it is not necessary to proceed with a step of "air removal" before closing the casing 2.

The bag and overpack unit is then stored in suitable conditions in order to preserve said biological product.

For example, the bag and overpack unit is arranged in a metal cassette before being plunged into liquid nitrogen in order to preserve the biological product at −196° C.

While the present invention has been particularly described, it is evident that many alternatives, modifications and variations will be apparent to those skilled in the art in light of the foregoing description. It is therefore contemplated that the appended claims will embrace any such alternatives, modifications, and variations as falling within the true scope and spirit of the present invention.

The invention claimed is:

1. Kit for preserving a biological product comprising a bag (1) intended to hold said biological product, said bag (1) having a constant three-dimensional geometry during the use thereof, and a casing (2) intended to pack said bag, said casing (2) including a housing (3) arranged such as to receive said bag (1), characterised in that said housing (3) has a constant three-dimensional geometry during the use thereof, and in that a slot (4) is provided along one edge of said housing in order to enable the bag (1) to be inserted in said housing (3), a front strip (5) and a rear strip (6) extend on the outside away from said slot (4), said strips being intended to be combined with one another in order to hermetically seal said housing (3) of the casing (2).

2. Kit according to claim 1, characterised in that the inside dimensions of the geometry of said housing (3) correspond to the outside dimensions of the geometry of said bag (1) to be placed in the housing (3).

3. Kit according to claim 1, characterised in that said bag (1) and said housing (3) are formed respectively of a substantially planar front face (7, 8) and rear face (9, 10), connected together by lateral walls (11, 12), each of said faces and said walls of the bag and of said housing (3) being intended to be arranged facing one another.

4. Kit according to claim 3, characterised in that said bag (1) comprising on one of the lateral walls (11) at least one inlet (13) and/or outlet (14, 15) orifice of the biological product.

5. Kit according to claim 1, characterised in that the bag (1) comprises at least two compartments (27, 28) separated by a partition (29).

6. Kit according to claim 3, characterised in that said slot (4) is provided on one of said lateral walls (12) of the housing (3).

7. Kit according to claim 5, characterised in that the casing (2) is formed from a first sheet (35) and from a second sheet (36), with at least one of the sheets (35, 36) having a relief (37, 38) forming at least one portion of the housing (3) for the bag, with the two sheets (35, 36) being assembled together along a peripheral seal (39) surrounding said relief (37, 38), with the peripheral seal (39) having an interruption in order to form the slot (4) of the casing (2).

8. Kit according to claim 7, characterised in that the peripheral seal (39) extends over a portion of the periphery of the strips (5, 6).

9. Kit according to claim 7, characterised in that the relief (37, 38) comprises at least one cavity (41) corresponding to the partition (29) of said bag.

10. Kit according to claim 7 characterised in that the thickness of each of the sheets (35, 36) forming the casing is comprised between 0.20 and 0.70 mm.

11. Kit according to claim 7, characterised in that at least the relief (37, 38) of one of the sheets (35, 36) forming the casing (2) is carried out by thermoforming.

12. Kit according to claim 11, characterised in that each of the two sheets (35, 36) comprises a relief (37, 38) carried out by thermoforming.

13. Kit according to claim 11, characterised in that the thermoformed sheet or sheets (35, 36) are made of a flexible thermoplastic material.

14. Kit according to claim 1, characterised in that the casing (2) and/or the bag (1) are made of ethylene vinyl acetate or polyethylene or fluoropolymer.

15. Kit according to claim 1, characterised in that the bag (1) and the casing (2) are made of the same material.

16. A method for preserving a biological product comprising the steps of:
    filling a bag (1) having a three-dimensional geometry with a biological product to be preserved;
    providing a casing (2) formed from a first sheet (35) and a second sheet (36), wherein said first sheet (35) and said second sheet (36) have a first relief (37) and a second relief (38) respectively, wherein said first sheet (35) and said second sheet (36) are assembled together along a peripheral seal (39) surrounding said first relief (37) and said second relief (38);
    providing a housing (3) formed at least in part by at least one of said first relief (37) and second relief (38), said housing (3) having dimensions which correspond to the outside dimensions of the geometry of said bag (1) and wherein said housing (3) has a three-dimensional geometry during the use thereof;
    providing said casing (2) with a front strip (5) and a rear strip (6);
    placing said bag (1) in said housing (3);
    combining said front strip (5) and said rear strip (6);
    storing said bag (1) in said casing (2); and
    wherein the storing step further comprises storing said bag (1) in said casing (2) at a temperature of at least less than approximately 4° C., and wherein the combining step is performed by welding.

* * * * *